(12) United States Patent
Aisaka et al.

(10) Patent No.: US 6,506,745 B1
(45) Date of Patent: Jan. 14, 2003

(54) MEDICINAL COMPOSITIONS FOR TREATMENT OF ATRIAL FIBRILLATION

(75) Inventors: Kazuo Aisaka, Osaka (JP); Naoya Imagawa, Osaka (JP); Hisato Miyai, Osaka (JP); Satoshi Ogawa, Tokyo (JP)

(73) Assignee: Noboru Kaneko, Tokyo (JP)

( * ) Notice: Subject to any disclaimer, the term of this patent is extended or adjusted under 35 U.S.C. 154(b) by 0 days.

(21) Appl. No.: 09/869,428

(22) PCT Filed: Dec. 27, 1999

(86) PCT No.: PCT/JP99/07359

§ 371 (c)(1),
(2), (4) Date: Oct. 1, 2001

(87) PCT Pub. No.: WO00/38688

PCT Pub. Date: Jul. 6, 2000

(30) Foreign Application Priority Data

Dec. 28, 1998 (JP) .......................................... 10-373332

(51) Int. Cl.$^7$ ................................................ A61K 31/55
(52) U.S. Cl. ................................................ 514/211.09
(58) Field of Search ..................................... 514/211.09

(56) References Cited

FOREIGN PATENT DOCUMENTS

| EP | 467325 A2 | 1/1992 | |
| JP | 0285323 A1 | 10/1988 | |
| JP | 0565721 A1 | 10/1993 | |
| WO | 92/12148 A1 | 7/1992 | |
| WO | 00/38688 | 12/1999 | A61K/31/554 |

*Primary Examiner*—James H. Reamer
(74) *Attorney, Agent, or Firm*—Sughrue Mion, PLLC

(57) ABSTRACT

The present invention relates to a medical composition for atrial fibrillation treatment, comprising a compound represented by the following formula [I]:

Formula [I]

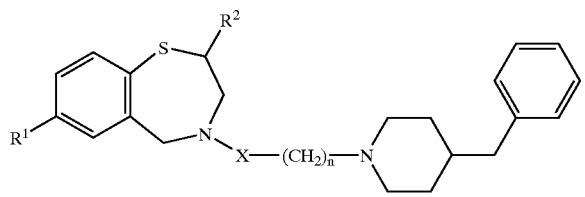

[wherein $R^1$ represents a hydrogen atom or lower alkoxy group; $R^2$ represents a hydrogen atom, lower alkoxy group or phenyl group (wherein the phenyl group may be substituted with 1 to 3 substituents selected from a group consisting of a hydroxides group and a lower alkoxy group),

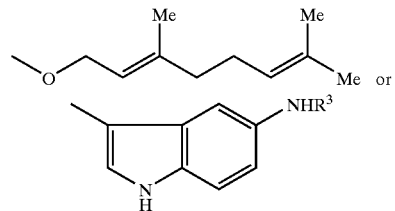

(wherein $R^3$ represents an acyl group); X represents —CO— or —CH$_2$—, and n represents an integer of 1 or 2.] The present invention also relates to a method of treating atrial fibrillation using said compound, and to the use of said compound for producing a medicine for atrial fibrillation treatment or salts thereof or prodrugs thereof.

3 Claims, 1 Drawing Sheet

MEDICINAL COMPOSITIONS FOR TREATMENT OF ATRIAL FIBRILLATION

TECHNICAL FIELD

The present invention relates to a medical composition for atrial fibrillation treatment to mammals including human, which includes 1,4-benzothiazepine derivatives. The present invention also relates to a method of treating atrial fibrillation using such derivatives and to the use of such derivatives for producing a medicine for atrial fibrillation treatment.

BACKGROUND ART

While atrial fibrillation is not a lethal arrhythmia, its morbidity is significantly high as 0.4 to 0.9% of the entire population,. and its frequency increases with aging. Such arrhythmia raises the risk rate of cerebral infarction up to about five times, and simultaneously deteriorates exercise capacity. Thus, the atrial fibrillation has been further emphasized as critical arrhythmia in conjunction with progressive increasing in elderly population.

Atrial fibrillation may be defined as a state when disordered excitation or activation is occurring frequently and irregularly in a small part of the atrium without harmonious excitation and construction of the entire atrium. Correspondingly, an electrocardiogram indicates waves having a baseline which fluctuates minutely and continuously (so-called "f wave"). This abnormal atrial activation is irregularly conducted to the ventricle through the atrio ventricular node. This causes completely irregular contractions in the ventricle, and absolute arrhythmia appears in pulsation. The arrhythmia includes transient (paroxysmal) arrhythmia which frequently occurs and perpetual arrhythmia.

As to their generation mechanism, the "Reentry" theory and "Ectopic Impulse Generation" theory have been suggested. However, it has not been achieved to explain all of the mechanism based on a single theory.

The term "Reentry" means a phenomenon such that once an occurred excitation is conducted through other cardiac regions and then excites the former region again. Once action potential is generated in a single myocardial cell, the resulting stimulation causes depolarization in adjacent cells, and this stimulation is conducted from one cell to another. Generally, myocardial cells are adapted not to be immediately re-excited due to its long refractory period after the action potential has been generated in one myocardial cell, so that the Reentry is not inherently worked out. Thus, it is required to satisfy the following four conditions to realize the Reentry;

(1) Presence of unidirectional block,
(2) Delay of conduction,
(3) Shortening of refractory period,
(4) Presence of Reentry path.

In these conditions, the presence of unidirectional block is most important. That is, if the conduction is bidirectional or both directions of the conduction are blocked, the Reentry cannot be realized. Excessive conduction velocity disenables the re-excitation because the refractory period is not passed over even if the excitation returns to the former region. Thus, the conduction is necessary to be tardy and slow. Further, shortened refractory period is advantageous to facilitate the establishment of the Reentry.

Diseases caused by atrial fibrillation include mitral valve pathology, ischemic heart disease, hypertension, various cardiomyopathies, constrictive pericarditis, and Basedow's disease. However, it is often the case that underlying diseases are not clear.

As to therapeutic agents for atrial fibrillation, Japanese Patent Laid-Open Publication No. Sho 49-000265 describes benzothiazole derivatives represented by the following formula;

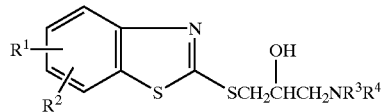

Japanese Patent Laid-Open Publication No. Sho 63-255278 (European Patent No.285323, U.S. Pat. No. 4,822,793) describes benzazepine derivatives represented by the following formula;

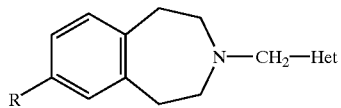

Japanese Patent Laid-Open Publication No. Hei 04-234386 (European Patent No. 467325, U.S. Pat. No. 5,082,847) describes carbostyril derivatives represented by the following formula;

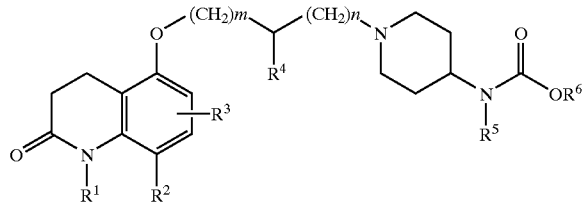

and Japanese Patent Laid-Open Publication No. Hei 09-169743 describes hexahydro-1H-1,4-diazepine derivatives represented by the following formula.

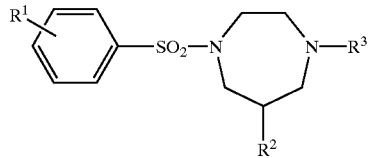

While another publications other than these documents describe various compounds, they do not describe 1,4-benzothiazepine derivatives as in the present invention.

On the other hand, Japanese Patent Laid-Open Publication No. Hei 04-230681 (International Publication No. WO92/12148, European Patent No. 565721, U.S. Pat. No. 5,416,066) describes 1,4-benzothiazepine derivatives or pharmaceutically acceptable salts represented by the following formulas and a manufacturing method thereof.

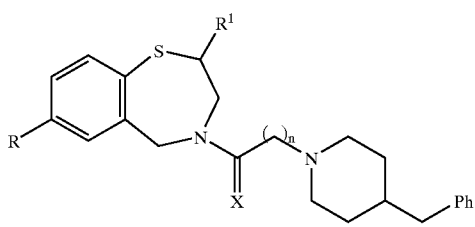

[wherein R represents a hydrogen atom or lower alkoxy group having 1 to 3 carbon atoms; $R^1$ represents a hydrogen atom, lower alkoxy group having 1 to 3 carbon atoms, or substituted phenyl group (wherein the substituent is a hydroxyl group or lower alkoxy group having 1 to 3 carbon atoms),

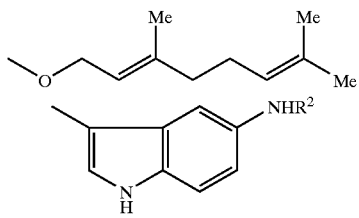

(wherein $R^2$ represents an acyl group); X represents an oxygen atom or H2; n represents an integer of 1 or 2; and Ph represents a phenyl group.]

According to the Japanese Patent Laid-Open Publication No. Hei 04-230681, it is described that there are two patterns of necrosis [Static cell death (SD) and Kinetic cell death (KD)] in myocardium of cardiac infarction patients and the major cell death in human cardiac infarction is classified into the KD. It is also described that the invented compounds have an excellent KD suppression effect. However, in this document, no description is included which suggests a certain application as therapeutic agents for atrial fibrillation treatment.

DISCLOSURE OF INVENTION

It is an object of the present invention to provide a therapeutic agent for atrial fibrillation treatment to mammals including human.

It is another object of the present invention to provide a method of treating atrial fibrillation to mammals including human.

As a result of a continuous research for achieving the above objects, the inventors have found out that a compound represented by the following formula [I] is amazingly excellent in anti-atrial fibrillation effects, and have completed the present invention.

The present invention is directed to a therapeutic agent for atrial fibrillation treatment, comprising a compound represented by the following formula [I] as an active component. The details will be shown as the following (1) to (7).

(1) A medical composition for atrial fibrillation treatment comprising a compound represented by the formula [I]:

Formula [I]

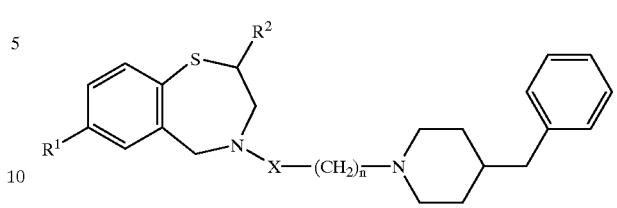

[wherein $R^1$ represents a hydrogen atom or lower alkoxy group; $R^2$ represents a hydrogen atom, lower alkoxy group or phenyl group (the phenyl group may be substituted with 1 to 3 substituents selected from a group consisting of a hydroxides group and a lower alkoxy group),

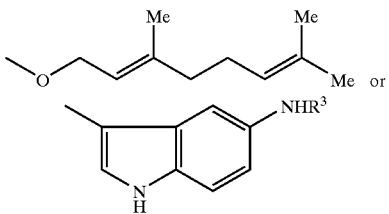

(wherein $R^3$ represents an acyl group); X represents —CO— or —CH2—, and n represents an integer of 1 or 2.] or salts thereof or prodrugs thereof; and a pharmaceutically acceptable carrier.

(2) A medical composition as defined in the above (1), wherein said compound is consisting of 4-[3-(4-benzylpiperidine-1-yl)propionyl]-7-methoxy-2,3,4,5-tetrahydro-1,4-benzothiazepine, salts thereof or prodrugs thereof.

(3) A method of treating atrial fibrillation comprising administering an effective amount of a compound represented by the above formula [I], salts thereof or prodrugs thereof.

(4) A method as defined in the above (3), wherein said compound is consisting of 4-[3-(4-benzylpiperidine-1-yl) propionyl]-7-methoxy-2,3,4,5-tetrahydro-1,4-benzothiazepine, salts thereof or prodrugs thereof.

(5) The use of a compound represented by the above formula. [I], salts thereof or prodrugs thereof, for producing a medicine for atrial fibrillation treatment.

(6) The use as defined in the above (5), wherein said compound is consisting of 4-[3-(4-benzylpiperidine-1-yl) propionyl]-7-methoxy-2,3,4,5-tetrahydro-1,4-benzothiazepine, salts thereof or prodrugs thereof.

(7) A commercial package comprising a medical composition as defined in the above (1) or (2) together with the printed matter relating to said medical composition, said instruction describing that said medical composition is useable or to be used for atrial fibrillation treatment.

DETAILED DESCRIPTION OF THE INVENTION

Figure 1:
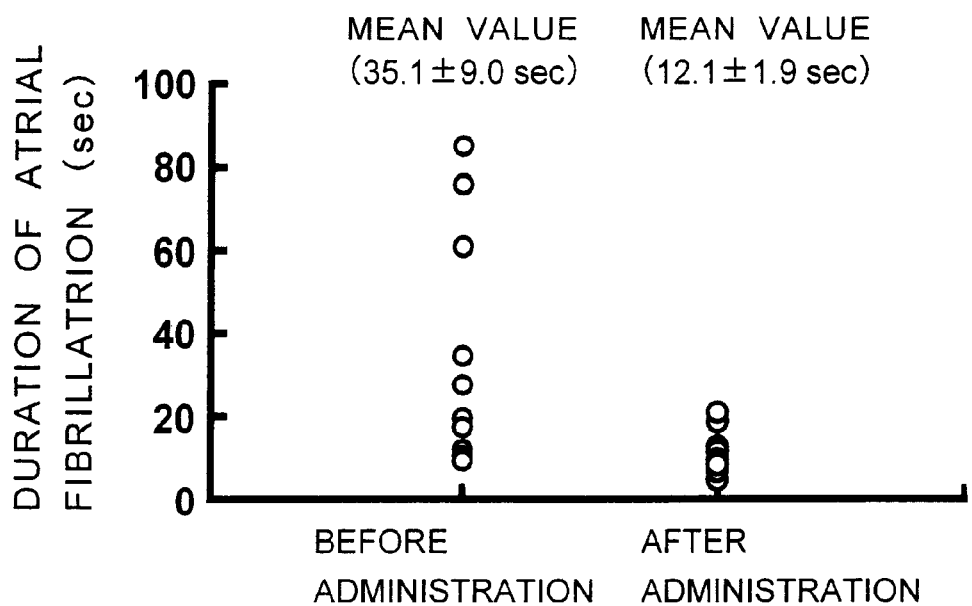
FIG. 1 is a graph representing an effect such that a compound 1 reduces a duration of an atrial fibrillation induced by means of electrical stimulation in example 3.

The terms used in this specification are defined as follows.

The "lower alkoxy group" means straight-chained or branched alkoxy groups having 1 to 6 carbon atoms. For example, the lower alkoxy group includes a methoxy group, ethoxy group, propoxy group, isopropoxy group, butoxy group, tert-butoxy group, pentyloxy group, tert-pentyloxy group or hexyloxy group, preferably, the methoxy group, ethoxy group, propoxy group or isopropoxy group, which has 1 to 3 carbon-atoms, more preferably, the methoxy group.

The "acyl group" includes a formyl group having 1 carbon atom; alkanoyl group having 2 to 6 carbon atoms, such as acetyl group, propionyl group, butyryl group, or pivaloyl group; or aryl group, such as benzoyl group, which may have 1 to 3 substituents on a aryl group. Preferably, the acyl group is the formyl group, acetyl groups, pivaloyl groups or benzoyl groups.

The "salts" of the compound shown in the formula [I] are pharmaceutically acceptable salts, and includes, but not limited to, an inorganic acid adduct salt, such as hydrochloride, hydrobromide, sulfate, phosphate, or nitrate; organic acid adduct salt, such as acetate, propionate, succinate, glycolate, lactate, malate, oxalate, tartrate, citrate, maleate, fumarate, methanesulfonate, benzenesulfonate, p-toluenesulfonate or ascorbate; and amino acid adduct salts, such as aspartate or glutamate. The salts may be hydrous materials or hydrates.

The "prodrugs" of the compound shown in the formula [I] is derivatives of the compound of the present invention, which have chemically or metabolically decomposable groups and exhibit pharmaceutical activities through hydrolysis, solvolysis or decomposition under physiological conditions.

In the compound shown in the formula [I] according to the present invention, preferably, the $R^1$ is a lower alkoxy group having 1 to 3 carbon atoms, and more preferably, a methoxy group. Preferably, the $R^2$ is a lower alkoxy group having 1 to 3 carbon atoms or a hydrogen atom, and more preferably, a hydrogen atom. Preferably, the X is —CO—. Preferably, the n is 2.

It is preferable that the compound represented by the formula [I] or the salts thereof is used as the active component of the medicines or medical composition for atrial fibrillation treatment.

The compound represented by the formula [I] according to the present invention may be produced based on the method described in Japanese Patent Laid-Open Publication No. Hei 04-230681 (International Publication No. WO092/12148, European Patent No. 565721, U.S. Pat. No. 5,416,066).

The compound represented by the formula [I] according to the present invention has an excellent anti-atrial fibrillation effect. When the compound of the present invention is used for atrial fibrillation treatment, it is typically administered generally or locally in oral or parenteral manner.

While the administered amount of the compound is varied depending on age, body weight, symptom, effectiveness, treatment time and others, the compound is typically administered in the range from 0.01 mg to 1 g per adult patient in oral or parenteral manner, once or several times a day.

The method of atrial fibrillation treatment of the present invention comprises administrating the effective amount of the compound represented by the formula [I], the salts thereof or the prodrugs thereof to mammals, preferably to human, necessary to be treated.

The compound represented by the formula [I] according to the present invention, the salts thereof or the prodrugs thereof may be administered in forms of a medical composition with a pharmaceutically acceptable carrier.

In case that the compound of the present invention is formed in a solid composition for oral administration, any suitable form, such as tablet, pill, powder or granule may be applied. In such a solid composition, one or more active materials are mixed with at least one inactive diluent, dispersant or absorbent, such as lactose, mannitol, glucose, hydroxypropyl cellulose, microcrystalline cellulose, starch, polyvinylpyrrolidone, magnesium alminate metasilicate or silicic acid anhydride powder. Any suitable additives other than diluents may be mixed with the composition in accordance with ordinary manners.

In case that the compound is prepared as a tablet or pill, the compound may be coated with a film formed of a material soluble in stomach or intestine, such as white sugar, gelatin, hydroxypropyl cellulose or hydroxymethyl cellulose phthalate, and may be coated with two or more layers. Further, the compound may be capsulated in a material, such as gelatin or ethylcellulose.

In case that the compound is formed in a liquid composition for oral administration, any pharmaceutically acceptable form, such as an emulsion, solvent, suspension, syrup or elixir may be applied. The applied diluent may include purified water, ethanol, plant oils or emulsifier and so on. In addition to diluents, this composition may be mixed with an auxiliary agent, such as a wetting agent, suspension, edulcorant, flavors, aromatic, or preservative.

In case that the compound is prepared as injection for parenteral administration, a sterile aqueous or non-aqueous solvent, solubilizer, suspension, or emulsifier is used. The aqueous solvent, solubilizer or suspension may, for example, include a water for injection, distilled water for injection, physiological salt solution, cyclodextorin and derivatives thereof, organic amine, such as triethanolamine, diethanolamine, monoethanolamine, or triethylamine, or inorganic alkaline solution.

In case of preparing as water-soluble solution, propylene glycol, polyethylene glycol, plant oils such as olive oil, or alcohol such as ethanol or the like may be applied. For solubilizer, surfactant such as polyoxyethylene hardened castor oil or sugar fatty acid esters (to form mixed micelle), or lecithin or water added lecithin (to form liposome) may be applied. Further, the compound may be prepared as an emulsion formed of a non-aqueous solvent such as plant oils, lecithin, and polyoxyethylene hardened castor oil or polyoxyethylene-polyoxypropylene-glycol.

Another composition for parenteral administration includes a liniment such as external solution or ointment, suppositories, or pessary, which includes one or more active materials and are prescribed through a well-known method.

EXAMPLE

Now, examples of preparation of a compound of the present invention will be described.

For a compound as preparation, 4-[3-(4-benzylpiperidine-1-yl)propionyl]-7-methoxy-2,3,4,5-tetrahydro-1,4-benzothiazepine (hereinafter, referred to as Compound 1) was used.

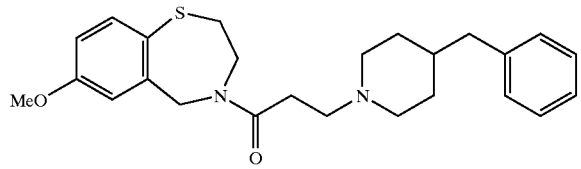

Example 1

Preparation for Injection

Compound 1 2~40 mg

D-sorbitol 1000 mg citric acid 10 mg sodium hydroxide proper quantity

Water for injection is added to these materials, to thereby prepare 20.0 ml of solution.

D-sorbitol and citric acid were dissolved in a sufficient amount of injection water. Compound 1 was dissolved in the resulting solution, and the solution was adjusted in pH of 3.2 to 3.3 by adding sodium hydroxide.

While stirring, the remaining injection water was added to the solution. The resultant solution was filtered and put into 20.0-ml ampoule, and sealed. Subsequently, the content of the ampoule was subjected to autoclave sterilization.

A pharmacological test of the inventive compound will be specifically described. Compound 1 was used as a subject compound.

Example 2

A beagle was used in the experimental test. Its right atrial. muscle was surgically extracted, and a sample was fixed with pins within an experimental vessel which is perfused with Tyrode liquid (10 ml/min). Using an electrical stimulator, the atrial muscle was stimulated by a voltage two times greater than that of generating an active potential, and rectangular waves having pulse. width of 2 msec in a frequency of 2 Hz, and the generated active potential was measured by a glass microelectrode inserted into the cells. Compound 1 was added into the experimental vessel with condensations of 0.3 µM and 1 µM. At 90 minutes before and after adding the compound, the sample was excited with various excitation frequencies, and each active potential was recorded to. determine the duration (90% recovery time; APD90). The result is shown in Table 1.

TABLE 1

| excitation frequency (Hz) | 0.3 µM | | 1 µM | |
|---|---|---|---|---|
| | duration before addition (msec) | change after addition (%) | duration before addition (msec) | change after addition (%) |
| 3.33 | 124.3 ± 6.08 | 111.5 ± 10.52 | 137.4 ± 9.52 | 124.7 ± 9.40 |
| 2 | 160.9 ± 13.62 | 113.0 ± 1.48 | 173.0 ± 9.17 | 118.1 ± 2.88 |
| 1 | 205.9 ± 9.95 | 110.1 ± 2.75 | 209.0 ± 18.40 | 111.3 ± 5.34 |
| 0.67 | 214.3 ± 6.96 | 106.0 ± 2.01 | 214.3 ± 20.31 | 112.9 ± 6.47 |

From the result of the table 1, it was proved that Compound 1 (0.3 µM and 1 µM) provided a longer duration of the active potential of the atrial muscle. This result shows that Compound 1 has an anti-atrial fibrillation effect.

Example 3

Figure 2:
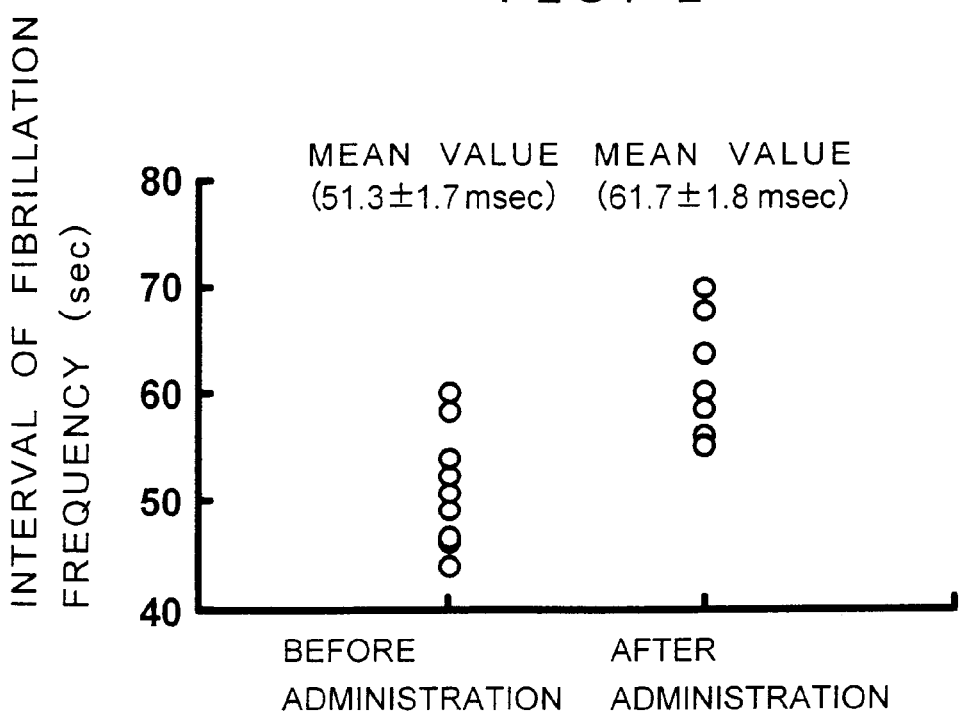
FIG. 2 is a graph representing an effect such that a compound 1 expands a time interval of an atrial fibrillation induced by means of electric stimulation in example 3.

In the experimental test, a hybrid of a labrador and beagle was used. An electrode for electrical excitation was embedded in the right atrium. From a week after the operation, the right atrium was subjected to a continuous pacing at an excitation frequency of 400 or 600 bpm by an external pacemaker. Further, for 31 day, the right atrium was subjected to a pacing giving a burst excitation (10 mA, 50 Hz, 1 sec) 5 days a week and several hours a day. Compound 1 was continuously injected into forearm vein (0.3mg/kg/min×2 min+0.03 mg/kg/min). At 20 minutes before and after administrating, the excitation current (50 Hz, 1 sec) was increased from 3 mA to 10 mA in increments of 0.5 mA to determine each atrial fibrillation threshold (AFT). Then, the atrial fibrillation duration (AF duration) and the interval (FF interval) of atrial fibrillation waves, which were generated by the excitation current of 10 mA, were measured. The result is shown in FIG. 1 and 2. In FIG. 1, the mean value of the AF duration before administration was 35.1±9.0 sec, and the mean value after administration was 12.1±1.9 sec. In FIG. 2, the mean value of the FF interval before administration was 51.3±1.7 msec, and the mean value after administration was 61.7±1.8 msec.

By virtue of the administration of Compound 1, the AFT was increased from 7 mA to 10 mA. In addition, the AF duration was reduced down to about one third as shown in FIG. 1, and the FF interval is additionally extended about 20% as shown in FIG. 2. From this result, it has been proved that Compound 1 had an anti-atrial fibrillation effect.

INDUSTRIAL APPLICABILITY

As is apparent from the above examples, the compound represented by the formula [I] according to the present invention has an excellent anti-atrial fibrillation effect to mammals including human. Thus, it is expected to provide a significantly effective therapeutic agent for atrial fibrillation.

This application is based on Japanese patent application No. Hei 10-373332 filed in Japan, and all of its contents are included in this application.

What is claimed is:

1. A method of treating atrial fibrillation comprising administering an effective amount of a compound represented by the following formula [I]:

[I]

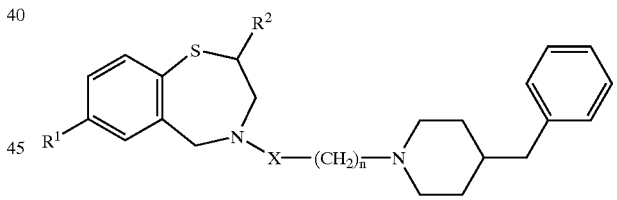

[wherein $R^1$ represents a hydrogen atom or lower alkoxy group; $R^2$ represents a hydrogen atom, lower alkoxy group or phenyl group (wherein the phenyl group may be substituted with 1 to 3 substitutents selected from a group consisting of a hydroxides group and a lower alkoxy group),

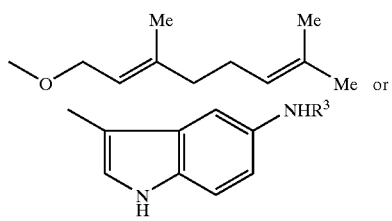

(wherein $R^3$ represents an acyl group); X represents —CO— or —CH$_2$—, and n represents an integer of 1 or 2 or salts thereof or prodrugs thereof.

2. A method as defined in claim 1 wherein said compound is consisting of 4-[3-(4-benzylpiperidine-1-yl)propionyl]-7-methoxy-2,3,4,5-tetrahydro-1,4-benzothiazepine, salts thereof or prodrugs thereof.

3. The use of a compound represented by the following formula [I]:

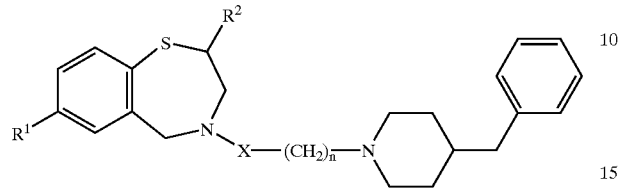

[wherein $R^1$ represents a hydrogen atom or lower alkoxy group; $R^2$ represents a hydrogen atom, lower alkoxy group or phenyl group (wherein the phenyl group may be substituted with 1 to 3 substituents selected from a group consisting of a hydroxides group and a lower alkoxy group),

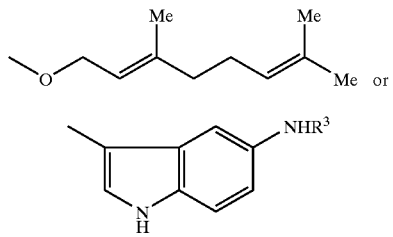

(wherein $R^3$ represents an acyl group); X represents —CO— or —CH$_2$—, and n represents an integer of 1 or 2 or salts thereof, for producing a medicine for atrial fibrillation treatment.

* * * * *